United States Patent

Ikeda et al.

[11] Patent Number: 5,902,806
[45] Date of Patent: May 11, 1999

[54] CRYSTALLINE VITAMIN D DERIVATIVE

[75] Inventors: Masahiko Ikeda, Ibaraki; Tomoko Uda, Hiroshima; Tohru Nakamura, Takatsuki, all of Japan

[73] Assignee: Sumitomo Pharmaceuticals Company, Limited, Osaka, Japan

[21] Appl. No.: 08/805,052

[22] Filed: Feb. 24, 1997

[30] Foreign Application Priority Data

Feb. 28, 1996 [JP] Japan .................................. 8-069468

[51] Int. Cl.$^6$ ...................... A01N 45/00; C07C 401/00
[52] U.S. Cl. ........................................ 514/167; 552/653
[58] Field of Search .............................. 514/167; 552/653

[56] References Cited

U.S. PATENT DOCUMENTS 5,030,626  7/1991  Hamma et al. ........................ 514/167

FOREIGN PATENT DOCUMENTS

| 0129003 | 12/1984 | European Pat. Off. | ......... A61K 7/48 |
| 0177920 | 4/1986 | European Pat. Off. | ....... A61K 31/59 |
| 0390930 | 10/1990 | European Pat. Off. | ....... A61K 31/59 |
| 63-183534 | 7/1988 | Japan | ............................. A61K 31/59 |
| 07126246 | 5/1995 | Japan . | |
| 07304733 | 11/1995 | Japan . | |
| WO8602527 | 5/1986 | WIPO | ............................ A01N 45/00 |
| WO9415912 | 7/1994 | WIPO | .......................... C07C 401/00 |

OTHER PUBLICATIONS

XP-002068116, *Proceedings of the Workshop on Vitamin D*, Honda et al., "Metabolism of 1,25–Dihydroxyvitamin $D_3$ and 26,26,26,27,27,27,–Hexafluoro–1, 25–Dihydroxyvitamin $D_3$ in HL–60 Cells," vol. 8, pp. 217–218, 1991.

J. Steroid Biochem. Molec. Biol. vol. 41, No. 1, pp. 109–112, 1992.

The Journal of the Osaka City Medical Center, vol. 42, No. 1, Mar. 1993, pp. 59–72.

The Japanese–United States Congress of Pharmaceutical Sciences, M03–Y–15(1987).

Komouro et al., Disposition and metabolism of ST–630. Yakubutsu Dotai, 1996, vol. 11, pp. 518–529, 1996.

Komouro et al., Disposition and metabolism of ST–630, Yakubutsu Dotai, 1996, vol. 11, pp. 530–540, 1996.

Igarashi et al., Kinetics of thermal [1,7]–sigmatropic shift of hexafluoro vit D3 and vitamin D3 derivatitives, Bioorg. Med. Chem. Lett., 1996, vol. 6, pp. 1431–1436, 1996.

Tanaka et al. Colon cancer and vitamin D, Seikagaku, 1996, vol. 68, pp. 214–219, 1996.

*Primary Examiner*—José G. Dees
*Assistant Examiner*—Alton Pryor
*Attorney, Agent, or Firm*—Birch, Stewart, Kolasch & Birch, LLP

[57] ABSTRACT

A crystalline (5Z,7E,23S)-26,26,26,27,27,27-hexafluoro-9,10-secocholesta-5,7,10(19)-trien-1α,3β,23,25-tetraol monohydrate has an excellent preservation stability, and is therefore useful as a medicine for treating or preventing bone diseases, tumor or psoriasis.

12 Claims, 1 Drawing Sheet

CRYSTALLINE VITAMIN D DERIVATIVE

BACKGROUND OF THE INVENTION

1. Field of the Invention

The present invention relates to a crystalline vitamin D derivative useful for treating or preventing a disease due to abnormality in calcium absorption, transportation or metabolism, tumor or psoriasis, a method for preparing the derivative and a medical use thereof. Further, the present invention relates to a stable pharmaceutical composition containing the vitamin D derivative.

2. Description of the Related Art

As one of vitamin D derivatives, (5Z,7E,23S)-26,26,26, 27,27,27-hexafluoro-9,10-secocholesta-5,7,10(19)-trien-1α,3β,23,25-tetraol of formula (2):

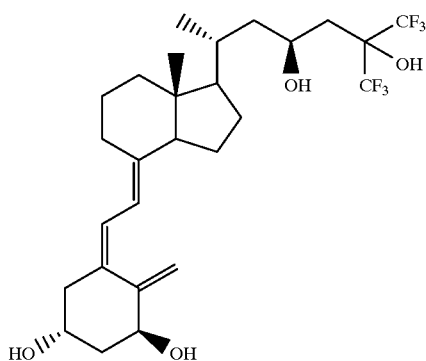

(2)

is known to be useful as a medicine for treating or preventing various bone diseases due to abnormality in calcium absorption, transportation or metabolism (for example, rickets, osteomalacia and osteoporosis), tumor or psoriasis (Japanese Patent KOKAI (Laid Open) No. 63-45249 and U.S. Pat. No. 5,030,626).

Neither Japanese Patent KOKAI (Laid-Open) No. 63-45249 nor U.S. Pat. No. 5,030,626 specifically disclose a vitamin D derivative hydrate, although they specifically disclose the vitamin D derivative in the form of non-crystal which is amorphous or non-crystalline powder.

In the meantime, it is known that an activated vitamin D is topically administered in the form of an external formulation to treat intractable skin diseases including psoriasis (EP 129003, EP 177920, WO 86/02527 and Japanese Patent KOKAI (Laid-Open) No. 63-183534).

The vitamin D derivative of formula (2) has such problems as poor preservation stability and difficult handling in preparation of a pharmaceutical formulation.

In general, an activated vitamin D is chemically unstable, particularly under the exposure of light. Thus, when administered in the form of an external formulation, the activated vitamin D is particularly unstable in the therapeutical use.

Accordingly, it is important to provide a pharmaceutical composition containing an activated vitamin D wherein the vitamin D is stable even under the exposure of light after externally administered.

SUMMARY OF THE INVENTION

The inventors of the present application have intensively researched to solve the problems as stated above and found out that a monohydrate of the vitamin D derivative of formula (2) in the form of crystal is extremely excellent in preservation stability. Further, the inventors have found out a stable pharmaceutical composition containing the vitamin D derivative. Thus, the present invention has been completed and accomplished.

Accordingly, an object of the present invention is to provide a crystalline vitamin D derivative of formula (1):

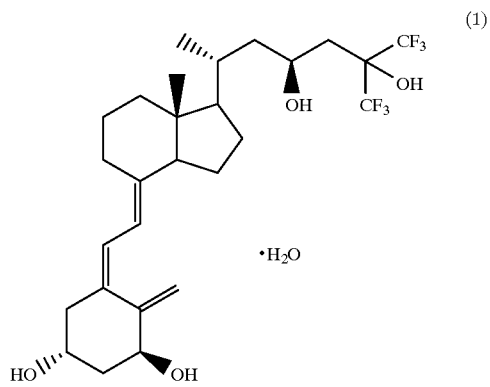

(1)

Another object of the present invention is to provide a method for preparing a crystalline vitamin D derivative of formula (1), which comprises the step of:

subjecting a non-crystalline vitamin D derivative of formula (2):

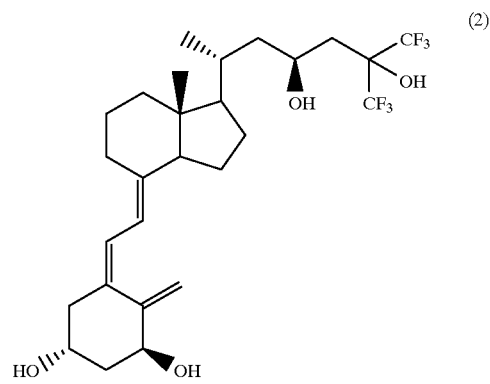

(2)

to crystallization treatment in an organic solvent having water added thereto.

Further, another object of the present invention is to provide a crystalline vitamin D derivative of formula (1) for therapeutical use.

Further, another object of the present invention is to provide a medicament comprising a crystalline vitamin D derivative of formula (1) as an active ingredient.

Further, another object of the present invention is to provide a medicament for the treatment or prophylaxis of a disease due to abnormality in calcium absorption, transportation or metabolism, tumor or psoriasis, which comprises a crystalline vitamin D derivative of formula (1) as an active ingredient.

Further, another object of the present invention is to provide a medicament for the treatment or prophylaxis of psoriasis, which comprises a crystalline vitamin D derivative of formula (1) as an active ingredient.

Further, another object of the present invention is to provide a pharmaceutical composition comprising a crystalline vitamin D derivative of formula (1) as an active ingredient and a pharmaceutically acceptable material.

Further, another object of the present invention is to provide a method for preparing a pharmaceutical composition which comprises the step of mixing a crystalline vitamin D derivative of formula (1) with a pharmaceutically acceptable material.

Further, another object of the present invention is to provide use of a crystalline vitamin D derivative of formula (1) in the preparation of a medicament or pharmaceutical composition for the treatment or prophylaxis of a disease due to abnormality in calcium absorption, transportation or metabolism, tumor or psoriasis.

DETAILED DESCRIPTION OF THE INVENTION

Figure 1:
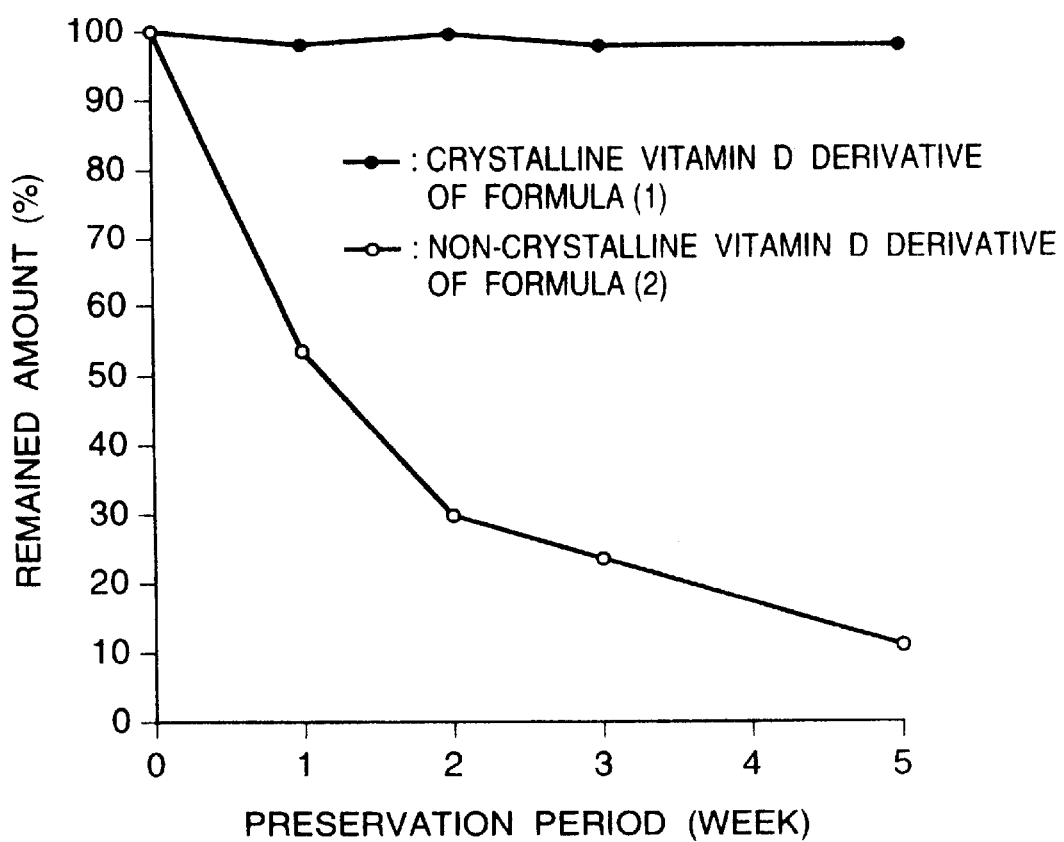
FIG. 1 shows the stability of the crystalline vitamin D derivative of formula (1) in atmosphere at room temperature without prevention of light-transmittance, as compared with that of the non-crystalline vitamin D derivative of formula (2).

The present invention provides the crystalline vitamin D derivative of formula (1), that is, crystalline (5Z,7E,23S)-26,26,26,27,27,27-hexafluoro-9,10-secocholesta-5,7,10 (19)-trien-1α,3β,23,25-tetraol monohydrate. The crystalline vitamin D derivative of formula (1) is extremely excellent in stability, and is therefore useful as a medicine for treating or preventing bone diseases, tumor or psoriasis.

The crystalline vitamin D derivative of formula (1) is preferably one showing a powder X-ray diffraction spectrum in average values of interplanar spacing d and relative intensity as given at Table 1 in Example 1 described hereinafter.

A method for preparing the crystalline vitamin D derivative of formula (1) is described below in detail.

The crystalline vitamin D derivative of formula (1) can be prepared by subjecting the non-crystalline vitamin D derivative of formula (2) to crystallizion treatment in an organic solvent having water added thereto.

The organic solvent includes aliphatic hydrocarbons such as n-pentane, n-hexane and n-heptane; aromatic hydrocarbons such as benzene and toluene; ethers such as diethyl ether, tetrahydrofuran and t-butylmethyl ether; ketones such as acetone, methylethyl ketone and methylisobutyl ketone; esters such as ethyl acetate; and mixtures thereof.

The organic solvent is preferably the aliphatic hydrocarbon, aromatic hydrocarbon, and mixture of the aliphatic hydrocarbon or aromatic hydrocarbon with the ether.

The crystallization treatment may be carried out by, for instance, dissolving the non-crystalline vitamin D derivative of formula (2) in the organic solvent at temperature of 10° C. to 35° C.; if necessary, distilling off partially the organic solvent; adding water thereto; and crystallizing the vitamin D derivative. The vitamin D derivative may be crystallized at temperature of 0° C. to 10° C.

Preferably, the non-crystalline vitamin D derivative is dissolved in a mixture of the aliphatic hydrocarbon or aromatic hydrocarbon with the ether, ketone or ester having a lower boiling point than that of the aliphatic hydrocarbon or aromatic hydrocarbon, then the ether, ketone or ester is distilled off, followed by addition of water to crystallize the vitamin D derivative. The aliphatic hydrocarbon or aromatic hydrocarbon may also be distilled off in order to raise yield of the crystalline vitamin D derivative.

The amount of the organic solvent after distilled off may be in the range of 5 to 200 parts by weight, preferably 8 to 100 parts by weight per part by weight of the non-crystalline vitamin D derivative.

Alternatively, water may be added to the organic solvent, before the non-crystalline vitamin D derivative is dissolved in the organic solvent.

When crystallizing the vitamin D derivative, seed crystals may be added thereto.

Water may be added in an amount of at least 0.1 part by weight, preferably 1 to 20 parts by weight per part by weight of the non-crystalline vitamin D derivative.

The period of time required for crystallizing the vitamin D derivative may vary depending on the crystallization speed, but is usually in the range of 30 minutes to 24 hours.

The thus obtained crystalline vitamin D derivative of formula (1) may be recovered by filtration. Upon recovery, the crystalline vitamin D derivative may be, if necessary, washed with the organic solvent as used in the crystallization treatment.

The crystalline vitamin D derivative of formula (1) according to the present invention may be subjected to dehydration under reduced pressure to produce a corresponding crystalline non-hydrate of the vitamin D derivative, namely, a crystalline vitamin D derivative of formula (2).

The crystalline vitamin D derivative of formula (1) exhibits the same pharmacological activities as those of the non-crystalline vitamin D derivative of formula (2), and is therefore useful as a medicine for therapy. More specifically, the crystalline vitamin D derivative of formula (1) is useful as a medicine for treating or preventing bone disease (for example, rickets, osteomalacia and osteoporosis) caused by abnormality in calcium absorption, transportation or metabolism, tumor, or psoriasis, likewise the non-crystalline vitamin D derivative of formula (2) as described in Japanese Patent KOKAI (Laid-Open) No. 63-45249 and U.S. Pat. No. 5,030,626.

A pharmaceutical composition may be prepared by mixing the crystalline vitamin D derivative of formula (1) with a pharmaceutically acceptable material.

The pharmaceutical composition may be in the form of an formulation for topical or systemical administration.

The formulation for topical administration may be an external formulation including liquids such as lotions, extracts, suspensions and emulsions; and semi-solids such as oleaginous ointments, emulsion ointments and water soluble ointments.

The external formulation is preferably used for treating or preventing psoriasis.

The formulation for systemical administration may be oral preparations in the form of tablets, granules, liquids, capsules or soft capsules, or other preparations such as injections, suppositories and nasal preparations.

When formulated into an external formulation, the crystalline vitamine D derivative of formula (1) may be contained in an amount of 1 ng to 1 mg, preferably 50 ng to 50 µg per unit weight of the pharmaceutical composition.

When systemically administered, the crystaline vitamin D derivative of formula (1) may be administered at a dose of 2 ng to 100 µg, preferably 10 ng to 20 µg per human adult per day.

The formulation may be prepared according to conventionally used methods.

A pharmaceutically acceptable material for preparing the external formulation may usually include bases, preservatives and antioxidants. Such bases include hydrocarbon such as mineral oils, solid paraffin, white soft paraffin, liquid paraffin, gelled hydrocarbon, dimethylpolysiloxan, olieve oil, sesami oil and medium chain triglycerides; aliphatic acid esters such as isopropyl myristate, diisopropyl adipate and diethyl sebacate; higher alcohols such as stearyl alcohol and cetyl alcohol; water soluble polyhydric alcohols such as propylene glycol, polyethylene glycol and glycerine; lower alcohols such as ethanol and isopropanol; surface active agents such as polyoxyethylene sorbitan fatty acid esters, glycerol esters and polyoxyethylene-hardened castor oil; and water. Such preservatives include 4-hydroxybenzoic acid esters. Such antioxidants include 2,6-di-t-butyl-4-methylphenol and 2-t-butyl-4-methoxyphenol.

The pharmaceutical composition may preferably have an ultraviolet light absorption agent added thereto. The ultraviolet light absorption agent may include benzophenones, 4-aminobenzoic acids, cinnamic acids, salicylic acids, anthranilic acids, vitamin Es, 1-(4-methoxyphenyl)-3-(4-t-butylphenyl)propan-1,3-dione, urocanic acids and camphor. Such benzophenones include 2-hydroxy-4-methoxybenzophenone, 2-hydroxy-4-methoxybenzophenone-5-sulphonic acid, sodium 2-hydroxy-4-methoxybenzophenone-5-sulphonate, 2,2'-dihydroxy-4,4'-dimethoxybenzophenone, disodium 2,2'-dihydroxy-4,4'-dimethoxybenzophenone-5,5'-disulphonate, 2,4-dihydroxybenzophenone and 2,2',4,4'-tetrahydroxybenzophenone. Such 4-aminobenzoic acids include 4-aminobenzoic acid, ethyl 4-aminobenzoate, glycerol 4-aminobenzoate, amyl 4-dimethylaminobenzoate and octyl 4-dimethylaminobenzoate. Such cinnamic acids include isopropyl 4-methoxycinnamate, ethyl 4-methoxycinnamate, 2-ethylhexyl 4-methoxycinnamate, 2-ethoxyethyl 4-methoxycinnamate, potassium 4-methoxycinnamate and sodium 4-methoxycinnamate. Such salicylic acids include octyl salicylate, phenyl salicylate and methyl salicylate. Such anthranilic acids include methyl anthranilate and homomentyl N-acetyl-anthranilate. Such vitamin Es include natural vitamin E, tocopherol acetate and dl-α-tocopherol. Such urocanic acids include urocanic acid and ethyl urocanate.

Those ultraviolet light absorption agents may be used singly or in combination therewith.

Particularly, 2-ethylhexyl 4-methoxycinnamate and tocopherol acetate are preferably used as the ultraviolet light absorption agent.

The amount of the ultraviolet light absorption agent used may be determined depending on the base used in the pharmaceutical composition, but preferably in the range of 0.01 to 2% by weight per by weight the pharmaceutical composition.

The present invention will be described in detail below, referring to Examples, which are not limitative of the present invention.

EXAMPLE 1

Preparation of Crystalline Vitamin D Derivative of Formula (1)

Ten mg of the non-crystalline vitamin D derivative of formula (2) was dissolved into 0.2 ml of diethyl ether, and 1.34 ml of toluene was added thereto. The resulting mixture was stirred to obtain a homogeneous solution. Then, the solution was concentrated to a half volume under reduced pressure, and three drops (about 100 mg) of purified water were added thereto. The solution was further stirred at room temperature for at least 15 hours. After cooling to about 5° C., the precipitated crystals were collected by filtration, whereby 7 mg of the crystalline vitamine D derivative of formula (1) was obtained. The thus obtained crystalline vitamin D derivative showed a powder X-ray diffraction spectrum as given in the following Table 1.

TABLE 1

Average values of interplanar spacing d and relative intensity

| Interplanar spacing d | Relative intensity | Interplanar spacing d | Relative intensity |
|---|---|---|---|
| 15.77 | 100 | 3.92 | 7 |
| 10.80 | 10 | 3.77 | 10 |
| 9.58 | 6 | 3.73 | 8 |
| 8.37 | 15 | 3.67 | 5 |
| 7.89 | 13 | 3.60 | 7 |
| 7.46 | 8 | 3.55 | 6 |
| 6.65 | 51 | 3.46 | 8 |
| 6.34 | 31 | 3.31 | 15 |
| 5.96 | 23 | 3.18 | 8 |
| 5.79 | 29 | 2.96 | 7 |
| 5.34 | 54 | 2.92 | 6 |
| 4.88 | 18 | 2.76 | 5 |
| 4.78 | 25 | 2.70 | 5 |
| 4.54 | 29 | 2.66 | 6 |
| 4.32 | 13 | 2.63 | 7 |
| 4.23 | 18 | 2.54 | 5 |
| 4.17 | 13 | 2.48 | 5 |

EXAMPLE 2

Preparation of Crystalline Vitamin D derivative of Formula (1)

Ten mg of the non-crystalline vitamin D derivative of formula (2) was dissolved into 0.3 ml of diethyl ether, and 0.5 ml of n-heptane was further added thereto. The resulting mixture was stirred to obtain a homogeneous solution. Then, three drops of purified water were added to the solution, and stirred at room temperature for at least 15 hours. The precipitated crystals were collected by filtration, whereby 6.5 mg of the crystalline vitamin D derivative of formula (1) was obtained.

EXAMPLE 3

Preparation of Crystalline Vitamin D Derivative of Formula (1)

Ten mg of the non-crystalline vitamin D derivative of formula (2) was dissolved into 0.3 ml of diethyl ether, and 0.5 ml of n-hexane was further added thereto. The resulting mixture was stirred to obtain a homogeneous solution. Then, three drops of purified water was added thereto, and stirred at room temperature for at least 15 hours. The precipitated crystals were collected by filtration, whereby 7 mg of the crystalline vitamin D derivatives of formula (1) was obtained.

EXAMPLE 4

Preparation of Crystalline Vitamin D Derivative of Formula (1)

1.56 g of the non-crystalline vitamin D derivative of formula (2) was dissolved into 14.4 ml of diethyl ether, and 15.6 ml of toluene was further added thereto. The resulting mixture was stirred to obtain a homogeneous solution. Then, the solution was concentrated to a half volume under reduced pressure. To the solution was added 5.23 ml of purified water and 5 mg of seed crystals, then stirred at room temperature for at least 15 hours. The precipitated crystals were collected by filtration, whereby 1.33 g of the crystalline vitamin D derivative of formula (1) was obtained.

EXAMPLE 5

Preparation of Crystalline Vitamin D Derivative of Formula (1)

Ten mg of the non-crystalline vitamin D derivative of formula (2) was dissolved into 0.5 ml of acetone, and 1.0 ml of toluene was further added thereto. The resulting mixture was stirred to obtain a homogeneous solution. Then, the solution was concentrated to a half volume under reduced pressure, and three drops of purified water was added thereto, followed by stirring at room temperature for at least 15 hours. The precipitated crystals were collected by filtration, whereby 7 mg of the crystalline vitamin D derivative of formula (1) was obtained.

EXAMPLE 6

Preparation of Crystalline Vitamin D Derivative of Formula (1)

Ten mg of the non-crystalline vitamin D derivative of formula (2) was dissolved into 0.2 ml of ethyl acetate, and 1.0 ml of toluene was further added thereto. The resulting mixture was stirred to obtain a homogeneous solution. Then, the solution was concentrated to a half volume under reduced pressure, and three drops of purified water was added thereto, followed by stirring at room temperature for at least 15 hours. The precipitated crystals were collected by filtration, whereby 5 mg of the crystalline vitamin D derivative of formula (1) was obtained.

EXAMPLE 7

Preparation of Crystalline Vitamin D Derivative of Formula (1)

Ten mg of the non-crystalline vitamin D derivative of formula (2) was dissolved into 0.2 ml of ethyl acetate, and 1.0 ml of n-hexane was further added thereto. The resulting mixture was stirred to obtain a homogeneous solution. Then, the solution was concentrated to a half volume under reduced pressure, and three drops of purified water was added thereto, followed by stirring at room temperature for at least 15 hours. The precipitated crystals were collected by filtration, whereby the crystalline vitamin D derivative of formula (1) was obtained.

EXAMPLE 8

Preservation Stability of Crystalline Vitamin D Derivative of Formula (1) and Non-Crystalline Vitamin D Derivative of Formula (2)

Each of the crystalline vitamin D derivative of formula (1) obtained in Example 4 and the non-crystalline vitamin D derivative of formula (2) was accurately weighed to obtain the vitamin D derivative at an amount in a range of about 1 mg to 1.5 mg. The vitamin D derivatives were preserved in atmosphere at room temperature without prevention of light-transmittance, for 1 to 5 weeks.

Thereafter, the preserved vitamin D derivatives were analyzed for the remained compound without decomposition according to a absolute calibration curve method using a high performance liquid chromatography. The obtained results are shown in FIG. 1. The results indicate that the crystalline vitamin D derivative of formula (1) almost remained without decomposition after the preservation, whereas the non-crystalline vitamin D derivative of formula (2) remarkably decomposed.

EXAMPLE 9

Preparation of Ointments 8.27 mg of the crystalline vitamin D derivative of formula (1) obtained in Example 4 was mixed with 0.498 g of 2,6-di-t-butyl-4-methylphenol, 1 g of 2-ethylhexyl 4-methoxycinnamate and 0.2 g of ethanol, followed by addition of isopropyl myristate to make the total amount 51 g. The resulting mixture was stirred, then fused with 949 g of white soft parrafin at 40° C. The mixture was cooled to room temperature with stirring to obtain 1000 g of ointments.

EXAMPLE 10

Preparation of External Liquids 2.07 mg of the crystalline vitamin D derivative of formula (1) obtained in Example 4 was mixed with 0.498 g of 2,6-di-t-butyl-4-methylphenol, 1 g of 2-ethylhexyl 4-methoxycinnamate and 0.2 g of ethanol, followed by addition of isopropyl myristate to make the total amount 51 g. The resulting mixture was stirred, and ethanol was added thereto to make the total volume 1000 ml. Thus, external liquids were obtained.

EXAMPLE 11

Preservation Stability of Pharmaceutical Composition

The ointments obtained in Example 9 were charged into aluminum tube, then preserved at room temperature for one year.

Thereafter, the ointments were analyzed for the remained crystalline vitamin D derivative of formula (1) according to an internal standard method using a high performance liquid chromatography. The obtained results showed that 100% of the crystalline vitamin D derivative of formula (1) remained in the ointments.

As described in detail hereinbefore, the crystalline vitamin D derivative of formula (1) according to the present invention is more excellent in preservation stability than the non-crystalline vitamin D derivative of formula (2), and can therefore be easily handled in preparing the pharmaceutical preparation. The crystalline vitamin D derivative according to the present invention can be obtained at high purity by a simple crystallization method.

Furthermore, the pharmaceutical composition according to the present invention is excellent in stability. Particularly, the external formulation containing an ultraviolet light absorption agent is extremely stable, and can preserve the vitamin D derivative without decomposition for a long period of time enough for therapeutical use, even under the exposure of light of 1000 Lux.

What we claim is:

1. A crystalline vitamin D derivative of formula (1):

2. A crystalline vitamin D derivative according to claim 1, which shows a powder X-ray diffraction spectrum in average values of interplanar spacing d and relative intensity as given in the following table:

| Inter-planar spacing d | Relative intensity | Inter-planar spacing d | Relative intensity |
|---|---|---|---|
| 15.77 | 100 | 3.92 | 7 |
| 10.80 | 10 | 3.77 | 10 |
| 9.58 | 6 | 3.73 | 8 |
| 8.37 | 15 | 3.67 | 5 |
| 7.89 | 13 | 3.60 | 7 |
| 7.46 | 8 | 3.55 | 6 |
| 6.65 | 51 | 3.46 | 8 |
| 6.34 | 31 | 3.31 | 15 |
| 5.96 | 23 | 3.18 | 8 |
| 5.79 | 29 | 2.96 | 7 |
| 5.34 | 54 | 2.92 | 6 |
| 4.88 | 18 | 2.76 | 5 |
| 4.78 | 25 | 2.70 | 5 |
| 4.54 | 29 | 2.66 | 6 |
| 4.32 | 13 | 2.63 | 7 |
| 4.23 | 18 | 2.54 | 5 |
| 4.17 | 13 | 2.48 | 5 |

3. A method for preparing a crystalline vitamin D derivative according to claim 1, which comprises the step of:

subjecting a non-crystalline vitamin D derivative of formula (2):

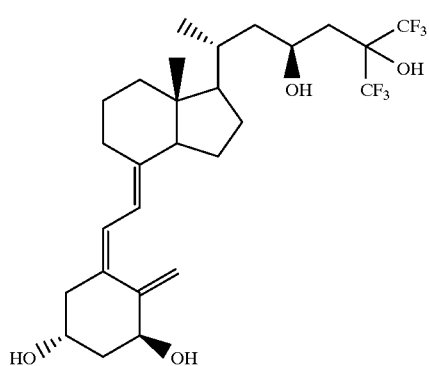

(2)

to crystallization treatment in an organic solvent having water added thereto.

4. A medicament for the treatment of a disease due to abnormality in calcium absorption, transportation or metabolism, tumor or psoriasis, which comprises an effective amount of a crystalline vitamin D derivative according to claim 1 as an active ingredient.

5. A medicament for the treatment of psoriasis, which comprises an effective amount of a crystalline vitamin D derivative according to claim 1 as an active ingredient.

6. A pharmaceutical composition comprising a crystalline vitamin D derivative according to claim 1 as an active ingredient and a pharmaceutically acceptable material.

7. A pharmaceutical composition according to claim 6, which is in the form of an external formulation.

8. A pharmaceutical composition according to claim 6, which contains an ultraviolet light absorption agent.

9. A pharmaceutical composition according to claim 8, wherein said ultraviolet light absorption agent is selected from benzophenones, 4-aminobenzoic acids, cinnamic acids, salicylic acids, anthranylic acids, vitamin Es, 1-(4-methoxyphenyl)-3-(4-t-butylphenyl)propan-1,3-dione, urocanic acids, and camphor.

10. A method for preparing a pharmaceutical composition which comprises the step of mixing a crystalline vitamin D derivative according to claim 1 with a pharmaceutically acceptable material.

11. A method of treating a disease caused by an abnormality in calcium absorption, transportation or metabolism, tumor or psoriasis, comprising administering to a person in need thereof, a pharmaceutical composition according to claim 6.

12. A method of treating psoriasis, comprising administering to a person in need thereof, a pharmaceutical composition according to claim 6.

* * * * *